United States Patent [19]

Ogino

[11] Patent Number: 5,479,939
[45] Date of Patent: Jan. 2, 1996

[54] SLEEP DETECTING APPARATUS

[75] Inventor: Hiroyuki Ogino, Nara, Japan

[73] Assignee: Matsushita Electric Industrial Co., Ltd., Osaka, Japan

[21] Appl. No.: 224,104

[22] Filed: Apr. 6, 1994

Related U.S. Application Data

[63] Continuation of Ser. No. 784,438, Dec. 20, 1991, abandoned.

[30] Foreign Application Priority Data

| Mar. 9, 1990 | [JP] | Japan | 2-058270 |
| Mar. 12, 1990 | [JP] | Japan | 2-60218 |
| May 25, 1990 | [JP] | Japan | 2-135893 |
| Jun. 20, 1990 | [JP] | Japan | 2-161822 |

[51] Int. Cl.⁶ ................................. A61B 5/103
[52] U.S. Cl. ................. 128/782; 340/575; 5/658
[58] Field of Search ................. 128/721, 722, 128/774, 782; 600/26–28; 340/573, 575; 5/658

[56] References Cited

U.S. PATENT DOCUMENTS

| 3,163,856 | 12/1964 | Kirby | 128/782 |
| 3,803,571 | 4/1974 | Luz | 340/573 |
| 3,898,981 | 8/1975 | Basham | 128/722 |
| 4,196,425 | 4/1980 | Williams, Jr. et al. | 340/573 |
| 4,295,133 | 10/1981 | Vance | 340/573 |
| 4,320,766 | 3/1982 | Alihanka et al. | 128/671 |
| 4,359,724 | 11/1982 | Zimmerman et al. | 340/575 |
| 4,665,385 | 5/1987 | Henderson | 340/539 |
| 4,665,926 | 5/1987 | Leuner et al. | 128/716 |
| 4,735,199 | 4/1988 | DiLullo | 128/782 |
| 4,836,219 | 6/1989 | Hobson et al. | 128/782 |
| 5,107,845 | 4/1992 | Guern et al. | 128/664 |
| 5,197,490 | 3/1993 | Steiner et al. | 128/782 |
| 5,266,807 | 11/1993 | Neiger | 250/353 |

FOREIGN PATENT DOCUMENTS

| 2451186 | 10/1980 | France . |
| 3133026 | 3/1983 | Germany . |
| 3248179 | 6/1984 | Germany . |
| 55-23614 | 6/1980 | Japan . |
| 57-30498 | 6/1982 | Japan . |
| 57-31902 | 7/1982 | Japan . |
| 58-27932 | 6/1983 | Japan . |
| 63283623 | 11/1983 | Japan . |
| 1236033 | 9/1989 | Japan . |
| 1238825 | 9/1989 | Japan . |

*Primary Examiner*—Stephen C. Pellegrino
*Assistant Examiner*—Guy V. Tucker
*Attorney, Agent, or Firm*—Cushman, Darby & Cushman

[57] ABSTRACT

Movement of a person in bed is detected without contacting the body, and time measurement is reset and started newly by a timer every time a detected movement exceeds a predetermined set value. When the measurement time of the timer exceeds a set time predetermined, it is judged that the body has fallen asleep on the bed. Meanwhile, absence or presence in bed and rough body movement are judged by detecting the fine body movement propagated by the functioning of heart and breathing of the body.

4 Claims, 16 Drawing Sheets

SLEEP DETECTING APPARATUS

This is a continuation of application No. 07/784,438, filed on Dec. 20, 1991, which was abandoned upon the filing hereof.

TECHNICAL FIELD

The present invention relates to a sleep detecting apparatus for detecting sleep.

Conventionally, this type of sleep detecting apparatus detects, for example, a brain wave and movement of eyes and processes the signal waveform detected to judge whether the subject has fallen asleep as shown in Japanese unexamined published Patent Application No. 62253034(1987)). Other apparatus detect a pulse wave of the body and processes the signal waveform to judge falling asleep, as in Japanese unexamined published patent application No. Sho 63-150047(1988). Both have, as shown in FIG. 1, detecting means 1 for detecting physical signals such as a brain wave, movement of the eyes and pulse wave, signal processing means 2 for processing the signal from the detecting means 1 and judging means 3 for judging whether the detectee has fallen asleep by using outputs from signal processing means 2.

Since the conventional configurations, however, are constructed such that the detecting means 1 for detecting the brain wave, movement of eyes and pulse waves are installed directly on the scalp or skin of the body, discomfort from the installation may disturb the sleeping patterns of the subject.

DISCLOSURE OF THE INVENTION

The present invention is designed to solve the above-mentioned problems, and therefore, it is a first object thereof to provide a sleep detecting apparatus which detects sleep easily without installing and annotating the detecting means to the human body, but by viewing the fact that movement of the body (hereinafter referred to as body movement) come to a standstill and sleep detects the body movement without contacting to the body to detect the sleep in response to of the quiescent time of the body movement.

It is a second object to show a specific configuration when an infra red-ray sensor is used in detecting the body movement without contact.

It is a third object to show a specific configuration wherein the body movement is detected by installing a piezo-electric element on bedding because movement of the portions such as hands and feet which are covered by the bedding can not be detected by the infra red-ray sensor.

It is a fourth object to show a specific configuration of a piezo-electric element which is suitable to be disposed on the bedding for detecting the body movement.

It is a fifth object to show a specific configuration in which the piezo-electric element is disposed removably on the bedding such that washing of the bedding is possible.

It is a sixth object to provide sleep detecting means which judges, first, whether there is the body on the bed so as not to make an erroneous detection as the body movement when things are placed on the bed or bed making is made, to judge the sleep.

It is a seventh object to detect the body movement reliably to detect sleeping by taking into account of an individual difference in the magnitude of body movement, allowing the user to set a set value for detecting the body movement optionally.

It is an eighth object to detect the body movement reliably to detect sleeping by taking into account of an individual difference in the magnitude of body movement, storing the magnitude of body movement successively to obtain the set value by learning.

It is a ninth object to detect the sleep reliably by taking into account of an individual difference in the quiescent time of the body movement, allowing the user to set a set time value of the body movement quiescent time optionally.

It is a tenth object to detect the sleeping reliably by taking into account of an individual difference in the quiescent time of the body movement, operating a frequency distribution of the body movement quiescent time to obtain the set time.

It is an eleventh object, in case the body movement is detected by a piezo-electric element to distinguish the movement of other in the vicinity of bed and vibration applied to the piezo-electric element by the bawdy movement of a person in bed.

It is a twelfth object to distinguish movement of other in the vicinity of bed and the body movement of the person in bed thereby to solve malfunction of the sleeping judgment, by detecting the body movement pulse rate of the person in bed.

It is a thirteenth object to show a configuration, whereby besides detecting the body movement using a weight sensor constituted by a load-cell as the body movement detecting means, detects weight to judge the presence and absence in bed.

In order to achieve the above-mentioned first object, the present invention consists of body movement detecting means for detecting movement of the body on the bed, a timer which resets time measurement and starts a new time measurement whenever a signal level of the body movement detecting means exceeds a first set value predetermined, and sleep judging means for judging that the body has fallen asleep when the measurement time of the timer exceeds a set time predetermined.

In order to achieve the second object, in the present invention, the body movement detecting means consists of an infra red-ray sensor which detects infra red rays, and is installed on a bed frame or on the wall of a room.

In order to achieve the third object, in the present invention, the body movement detecting means is constituted by, at least one piezo-electric element disposed on the bedding, a filter which filters a certain specific frequency component with respect to respective signals of the piezo-electric element, an amplifier which amplifies the filter signal, a rectifier which rectifies the amplifier signal and a smoothing device which smoothes the rectifier signal.

In order to achieve the fourth object, the present invention is constituted by a piezo-electric element consisting of a high-molecular piezo-electric material such as polyvinylidene fluoride, which is processed into a thin film and bonded with a flexible electrode film on both surfaces thereof to form a tape.

In order to achieve the fifth object, the present invention is that, the piezo-electric element is contained in a sheet shaped bag, and stretchingly-and-shrinkingly movable stretch-shrink parts are provided on the end parts of the bag, and in addition, engaging and disengaging parts, which enable engaging-and-disengaging of end tip parts of said stretch-shrink parts each other, are provided on respective ones of said end parts.

In order to achieve the sixth object, the present invention comprises: absence judging means for judging absence of the body on the bed when the signal level of the body movement detecting means is below a predetermined second set value; presence judging means for judging presence of the body on the bed in a quiet state, when the signal level is above the said second set value and below a third set value predetermined; and rough body movement judging means for judging a rough movement of the body such as turning over on the bed, when the signal level exceeds the third set value, a timer for resetting the time measurement whenever the absence or rough body movement is judged and starting the time measurement when the present in bed is judged.

In order to achieve the seventh object, the present invention provides display means for displaying the signal level of the body movement detecting means, and first setting means capable of manually changing over between the second set value and the third set value, basing on the signal level displayed by the display means.

In order to achieve the eighth object, the present invention comprises first memory means which samples and stores the signal level of the body movement detecting means at a predetermined period when the presence in bed is judged by the presence judging means, first operating means which operates a minimum value and a maximum value of the content stored in the first memory means, and second setting means which refreshes the minimum value as the second set value and the maximum value as the third set value.

In order to achieve the ninth object, the present invention comprises third setting means capable of setting the set time manually.

In order to achieve the tenth object, the present invention comprises second memory means for storing the measurement time of the timer whenever the time measurement of the timer is reset, second operation means for operating a frequency distribution of the measurement time stored in the second memory means, third operating means which operates to obtain a time T in a manner that the ratio of the cumulative frequency until the time T is the frequency distribution against the total cumulative frequency shows a certain predetermined value, and fourth setting means which executes the storing and operating operation at every fixed period thereby to refresh the setting with the time T as the set time.

In order to achieve the eleventh object, in the present invention, the body movement detecting means comprises at least one piezo-electric element disposed on the bedding, a filter which filters a certain specific frequency component for respective signals of the piezo-electric element, a first amplifier which amplifies the filter signal, a second amplifier having a smaller amplification than the first amplifier for amplifying the filter signal, a first smoothing device which smoothes the first amplifier signal, and a second smoothing device which smoothes the second amplifier signal, and further comprises absence judging means for judging absence of the body on the bedding when the signal level of the first smoothing device is below the second set value, presence judging means for judging presence of the body on the bedding in a quiet state when the signal level of the first smoothing device is above the second set value, and the signal level of the second smoothing device is below a fourth set value predetermined, and rough body movement judging means for judging the rough body movement of the body on the bedding when the signal level of the second smoothing device is above the fourth set value.

In order to achieve the twelfth object, the present invention comprises heart beat pulse rate detecting means for detecting and counting heart beat pulses by the signal of the body movement detecting means, third operating means for operating variation within a predetermined time of the heart beat pulse, and a timer which resets time measurement and starts the new measurement whenever the signal level of the body movement detecting means exceeds a predetermined fifth set value and the operation value of the third operating means exceeds a predetermined sixth set value.

Furthermore. in order to achieve the thirteenth object, in the present invention, the body movement detecting means comprises presence judging means which is consisting of a weight sensor using a load-cell and installed on the bedding and judges the absence and presence of a person on the bed by detecting weight of the person in bed by the weight sensor.

The present invention is operated in the following manner by the configuration stated hereinabove. Movement of the body present on the bedding is divided using the following two definitions. Let us call a very small movement of the body propagated from actions of the heart and breathing a fine body movement, and call the rough movement such as getting in and out of bed and turning over in bed a rough body movement.

When movement of the body on the bed is detected by the body movement detecting means, time measurement is reset and the new measurement is started by a timer every time the signal level of the body movement detecting means exceeds the predetermined first set value. Here, the first set value is set in advance to detect rough body movement. When the measurement time of the timer exceeds the predetermined set time, the sleep judging means determines that the human body has fallen asleep.

The present invention detects the body movement by an infra red-ray sensor disposed on a bedframe or on the wall of a room.

The present invention also outputs a voltage signal generated by piezo-electric effect, when at least a piezo-electric element disposed on the bedding is deformed by the body movement, after filtering, amplifying, rectifying and smoothing it in the smoothing device.

The present invention includes the above-mentioned piezo-electric element, which is constituted by processing a high-molecular piezo-electric material such as polyvinylidene fluoride into a thin film and bonding flexible electrode films on both faces thereof to form a tape.

The present invention also includes the piezo-electric element being contained in a sheet-shaped bag, on the portions of said sheet-shaped bag, and a stretchingly-and-shrinkingly movable stretch-shrink parts are provided on the end parts of the bag, and in addition, engaging and disengaging parts, which enable engaging-and-disengaging of end tip parts of said stretch-shrink parts each other, are provided on respective ones of said end parts.

The present invention includes an absence judging means which determines that the body is absent from the bed when the signal level of the weight detecting means is below a predetermined second set value. A judging means determines, that the body is on the bed in a quiet state when the said signal level is above the second set value and below the predetermined third set value, and judges by the rough body movement judging means that the body has moved roughly on the bed such as turning over when the signal level is above the third set value. The timer resets time measurement whenever the absence is judged or the rough body movement is judged and starts the measurement when the present in bed is judged, and when the measurement time of the timer exceeds a set time predetermined, the sleep judging means judges that the body has fallen asleep.

The present invention displays the signal level of the body movement detecting means and is able to change the second set value and the third set value manually in response to the signal level.

In the present invention, when the presence in bed is judged by the presence judging means, the signal level of the body movement detecting means is sampled and stored at a predetermined interval; and further a minimum value and a maximum value of the memory content are operated hence to refresh the minimum value as the second set value and the maximum value as the third set value by the second setting means.

The present invention is capable of setting the set time manually by the third setting means.

The present invention stores the measurement time of the timer and operates the frequency distribution of the measurement time every time the time measurement of the timer is reset, operates the time T in a manner that the ratio of cumulative frequency until the time T in the frequency distribution to the total cumulative frequency shows a predetermined certain value, and refreshes the setting taking the time T as the set time.

The present invention filters a signal of at least one piezo-electric device disposed on the bedding, amplifies the filtered signal respectively using two amplifiers having different amplifications, and rectifies and smoothes them. Then, distinguishing vibration propagated to the piezo-electric element by movement of other in the vicinity of the bed, and vibration applied to the piezo-electric element by the body movement of a person in bed, and judges the absence, presence and rough body movement to judge whether the person is sleeping.

The present invention detects and counts heart beat pulses by resetting the time measurement and starts a new measurement every time the signal level of the body movement detecting means exceeds a fifth set value and the change in heart beat pulse rates within a predetermined time exceeds a predetermined sixth set value. Then, it distinguishes vibration propagated to the piezo-electric element by movement of other in the vicinity of the bed, and vibration applied to the piezo-electric element by the body movement of a person in bed, and judges sleep accordingly.

Furthermore, the present invention detects weight of a person in bed by a load-cell installed on the bedding or a bed frame to judge the presence and absence in bed, and further, detects the body movement when the person is in bed to judge sleep.

BEST MODE FOR CARRYING OUT THE INVENTION

Figure 1:
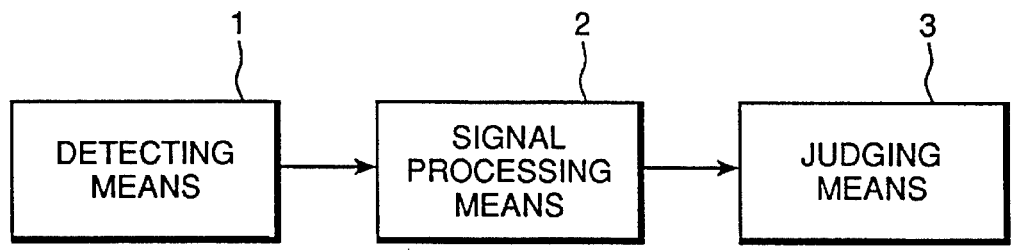
FIG. 1 is a block diagram of the conventional sleep detecting apparatus.
Figure 2:
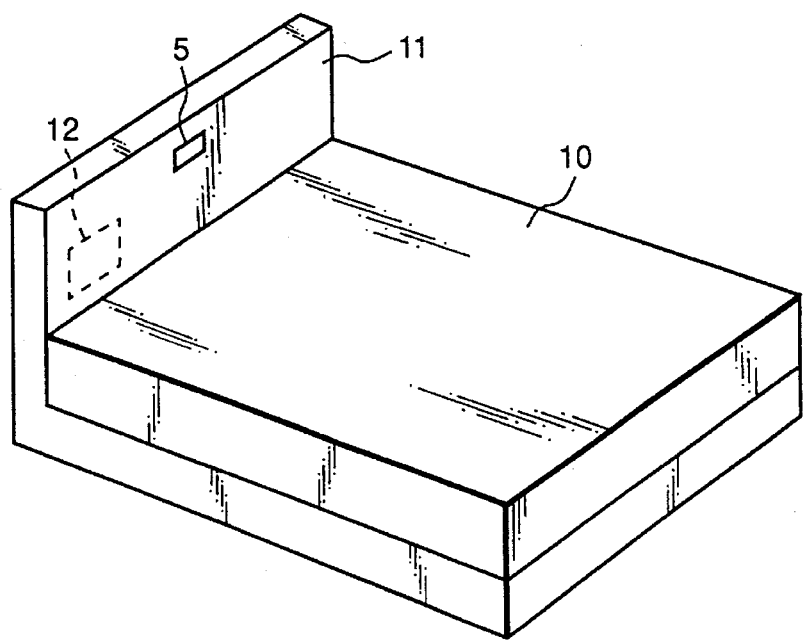
FIG. 2 is an external perspective view of a sleep detecting apparatus in a first working example of the present invention.
Figure 3:
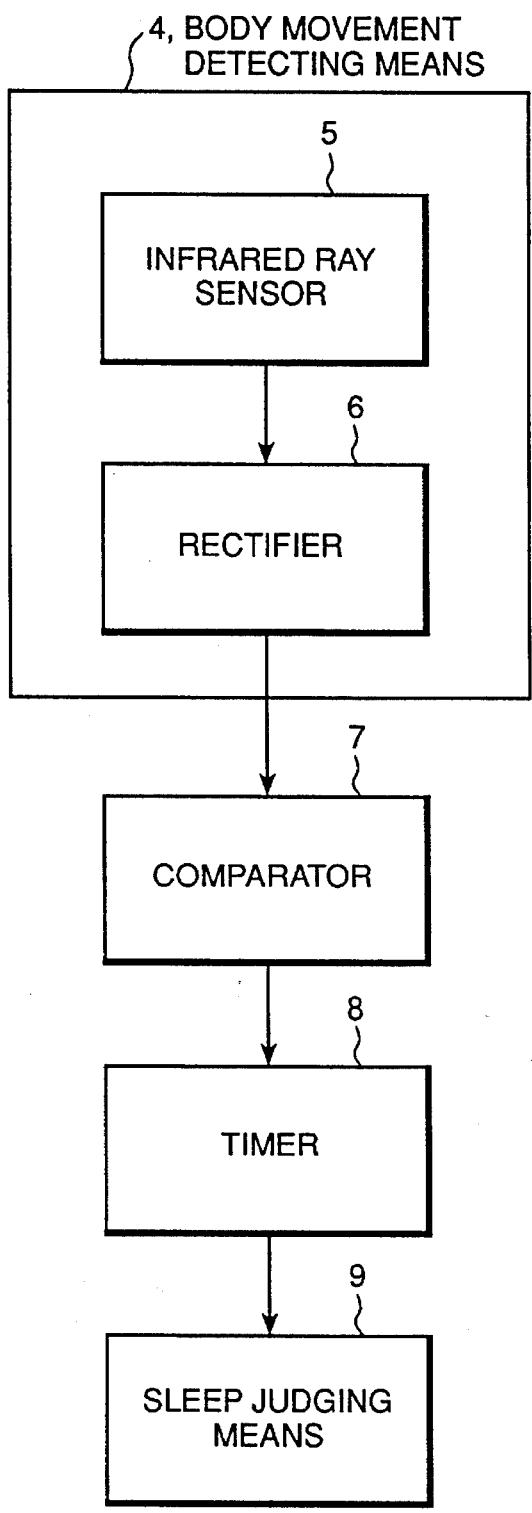
FIG. 3 is a block diagram showing a signal processing system of the apparatus of the first working example.

In the following, a first working example of the present invention will be described with reference to the accompanying drawings. FIG. 2 is a perspective view when the working example is installed on bed, and FIG. 3 is a block diagram. In FIG. 3, numeral 4 designates body movement detecting means consisting of an infra red-ray sensor 5 and a rectifier 6, numeral 7 designates a comparator numeral 8 designates a timer and numeral 9 designates sleep judging means. The infra red-ray sensor 5 is disposed on a bed board 11 of a bed 10. The rectifier 6, comparator 7, timer 8 and sleep judging means 9 are contained in a circuit unit 12.

Figure 4:
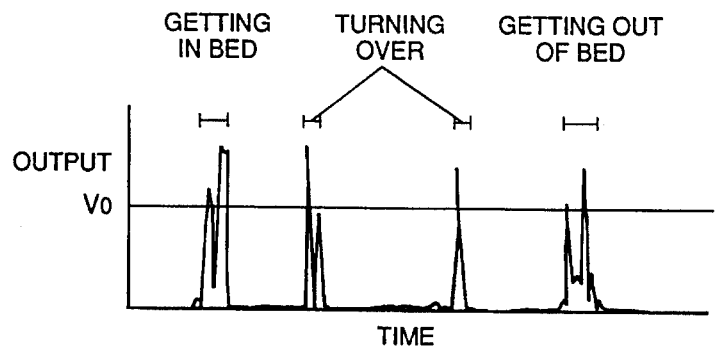
FIG. 4 is an output waveform diagram of a rectifier of the apparatus.

The above-mentioned configuration detects rough body movement such as turning over as produced by a person on the bed 10. A signal corresponding to the magnitude of body movement is generated from the infra red-ray sensor 5 and rectified by the rectifier 6. FIG. 4 shows an output waveform from the rectifier 6 during actual sleep. Whenever the signal of the rectifier 6 exceeds a predetermined first set value $V_0$ such as the case of turning over, time measurement is reset in the timer 8; and thereafter, the time measurement is newly started when the signal level drops below $V_0$. The sleep judging means 9 concludes that the body has fallen asleep when the measurement time of the timer 8 exceeds a predetermined set time $T_0$.

Figure 5:
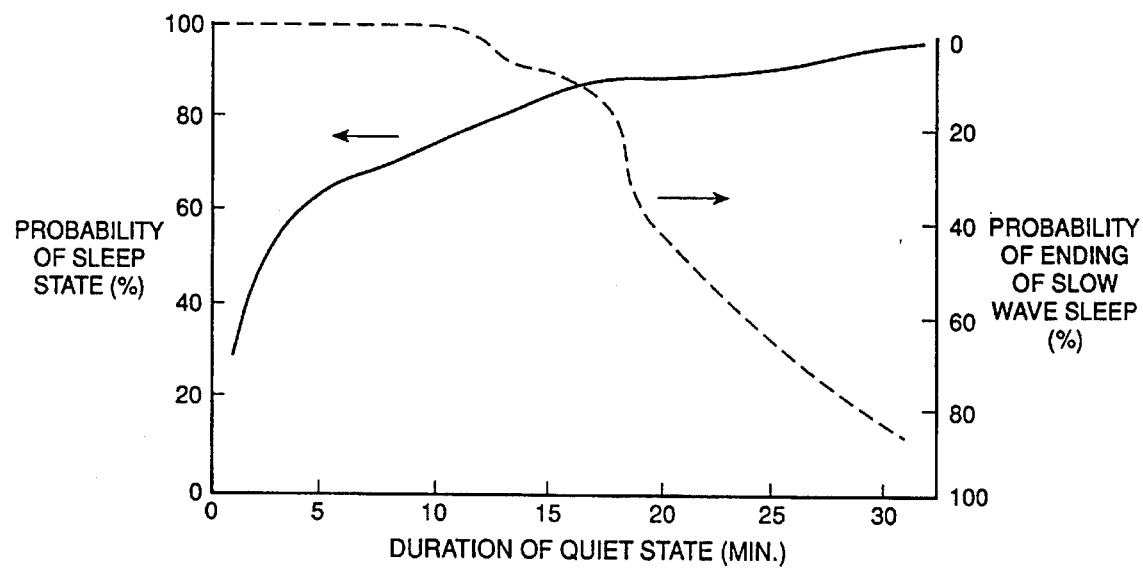
FIG. 5 is a characteristic diagram showing the relationship between a duration of quiet state and probability of the sleeping state.

In order to decide the set time $T_0$, we made the following study, about the relationship between rough body movement and a sleeping state. That is, by knowing that the rough body movement disappears when the person is sleeping, the relationship is obtained by experiment between a duration of quiet state where there is no rough body movement and probability of sleep of a person in bed in that state. The result is shown in FIG. 5. In the figure, the duration of quiet state is plotted along the abscissa, and probability of sleep of the person who is tested against the duration of quiet state is plotted along the left ordinate. In general, after a person falls asleep, it moves to a slow wave sleep which is deep sleep, and after some time, the rough body movement takes place and the slow wave sleep comes to an end. From this the probability of occurrence of the rough body movement and completion of the slow wave sleep when the quiet state has continued for some time is plotted along the right side ordinate. When the quiet state lasts for 15 minutes, there is about an 85% probability of sleep and 10% probability of end of the slow wave sleep. Thus, it is possible to judge sleep at a sufficient level for practical use by measuring the duration of the quiet state. 10 to 15 minutes are adequate for the above-mentioned set time $T_0$.

The body movement is detected by the infra red-ray sensor without contacting the body, and the sleep is judged from a simple variable such as a duration of the quiet state wherein the rough body movement is stopped by the operation stated above, so that the sleep can be easily detected without installing detecting means for detecting the brain wave and movement of eyes of the body as in the past.

Though the infra red-ray sensor was installed on a head-board of the bed in the aforesaid working example, it may be so constructed that the infra red-ray sensor is disposed on the wall surface of a room, as far as it is within a range where it detects movement of a person in bed.

Figure 7:
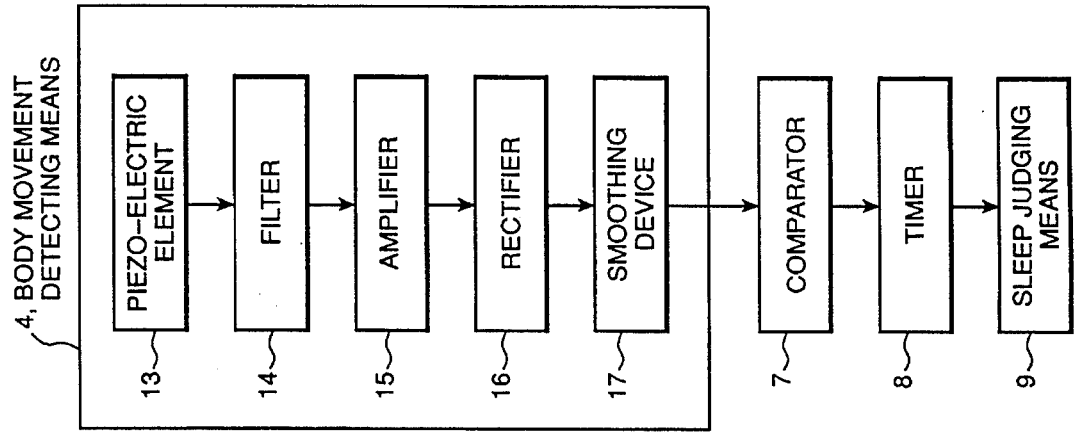
FIG. 7 is a block diagram showing a signal processing system of the apparatus of the second working example.
Figure 6:
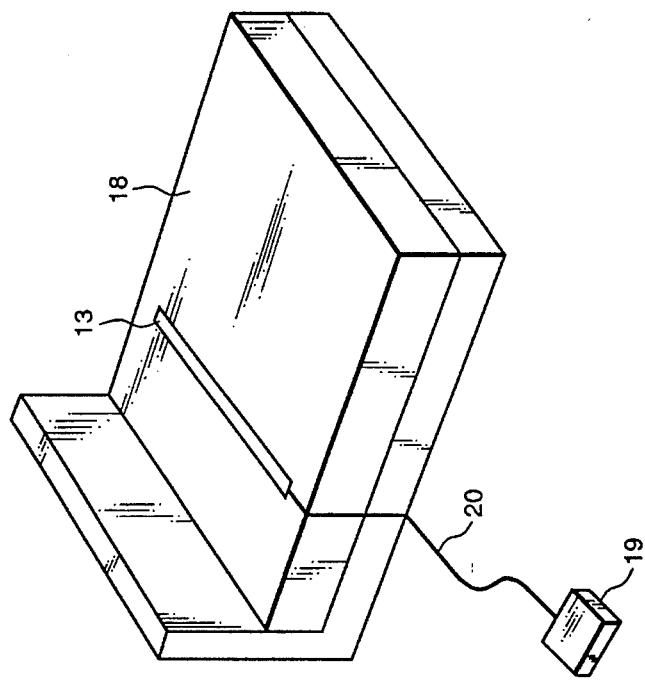
FIG. 6 is an external perspective view of a sleep detecting apparatus in a second working example of the present invention.

A second working example of the present invention will be described in the following. This working example differs from the aforesaid working example in using a body movement detecting means 4 constituted by a piezo-electric element 13, filter 14, amplifier 15, rectifier 16 and smoothing device 17 as shown in FIG. 6 and FIG. 7. The piezo-electric element 13 is constituted by a high-molecular material such as polyvinylidene fluoride which is processed into a thin film and bonded with a flexible electrode film on both surfaces thereof to form a tape, and is fixed on the surface of a mattress 18 as shown in FIG. 6. Numeral 19 designates a circuit unit wherein the filter 14, amplifier 15, rectifier 16, smoothing device 17, comparator 7, timer 8 and sleep judging means 9 (none of which is shown in , FIG. 6) are contained. The piezo-electric element 13 and the circuit unit 19 are connected with a shielded wire 20.

Figure 8:
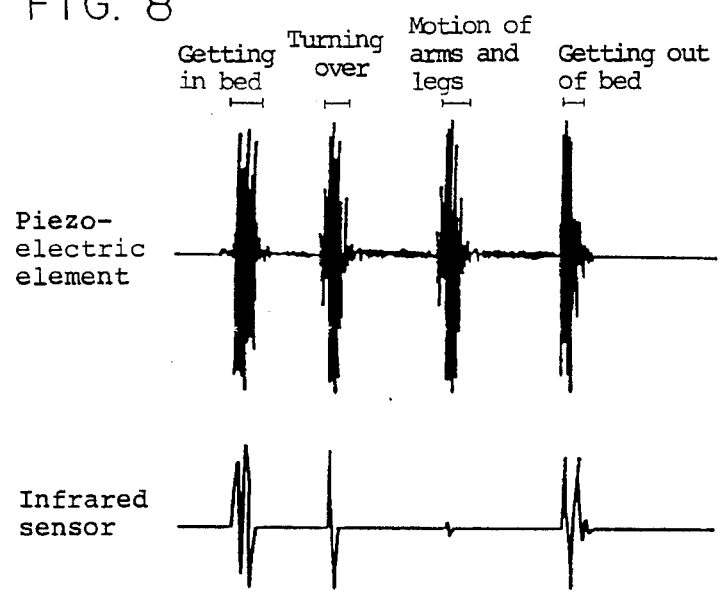
FIG. 8 is an output waveform diagram of a piezo-electric element of the present apparatus.
Figure 18:
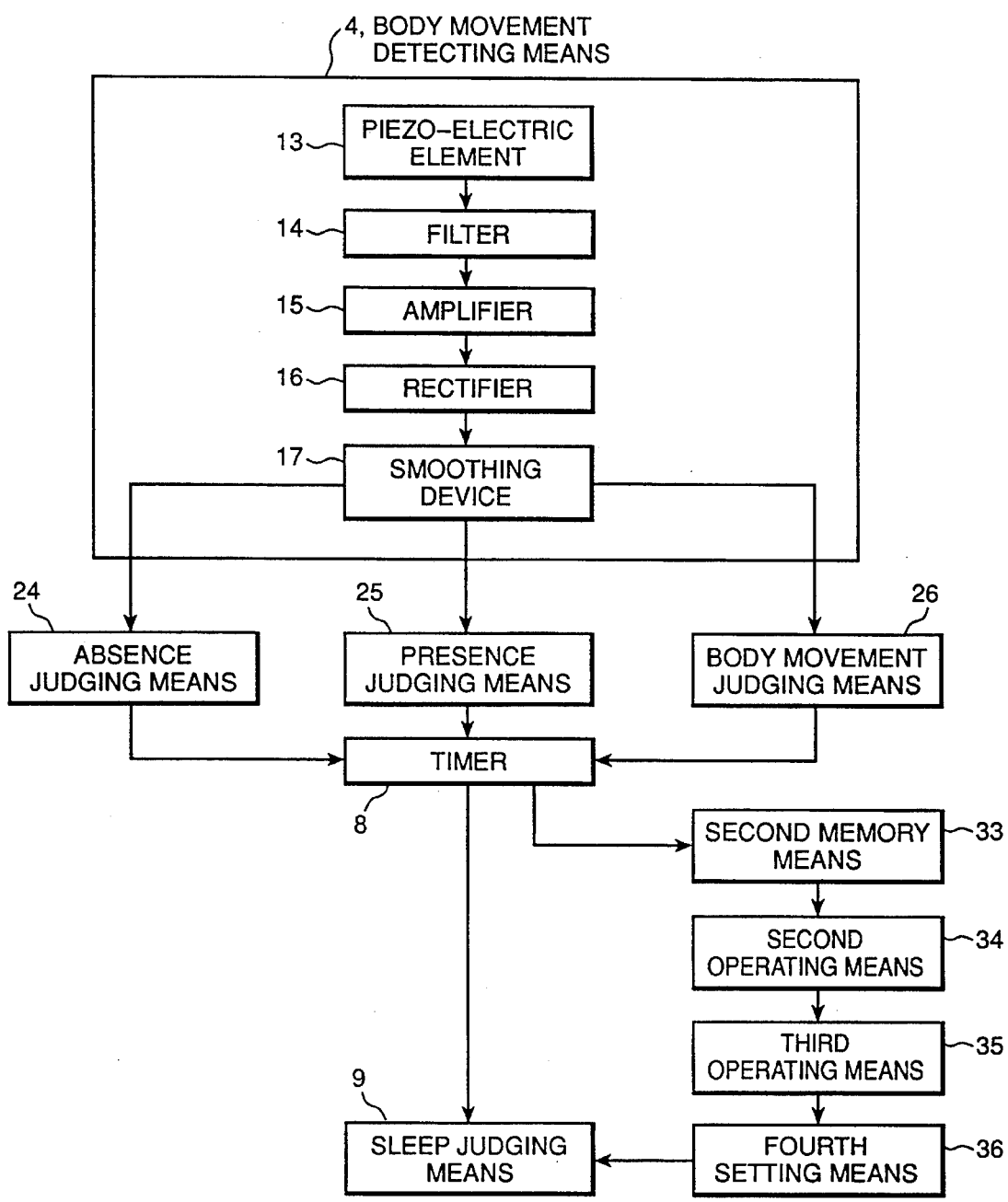
FIG. 18 is a block diagram showing a signal processing system of a sleep detecting apparatus in an eighth working example of the present invention.

According to the configuration of the working example stated above, when the body is present on the bed, when the piezo-electric element 13 is deformed by the fine body movement and rough body movement of the body as aforementioned, responsive to a degree of deformation a voltage is produced from the piezo-electric element 13. FIG. 18 shows an actual output signal from the piezo-electric element 13 and an output waveform from the infra red-ray sensor of the aforesaid working example. In FIG. 8, a high level signal from the piezo-electric element indicates rough body movement, such as getting in and out of the bed, turning over and movement of hands and feet. In the case of movement of hands and feet the signal from the infra red-ray sensor is not confirmed. This is because that portions such as hands and feet covered by the bedding can not be detected by the infra red-ray sensor. Next, about 1 to 10 Hz components of the output signal of the piezo-electric element 13 are filtered in the filter 14, and after being amplified by the amplifier 15, are rectified by the rectifier 16 and smoothed by the smoothing device 17.

Figure 9:
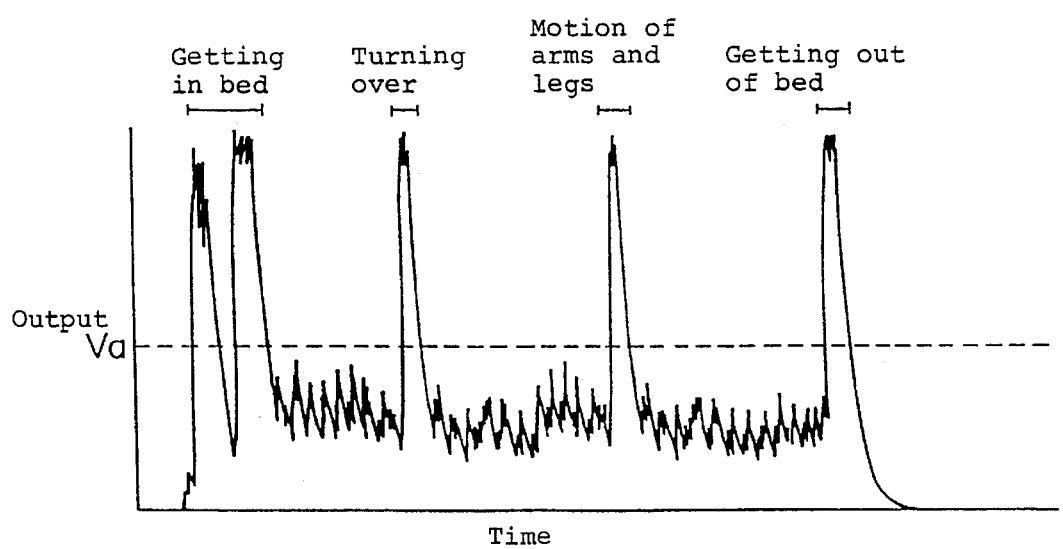
FIG. 9 is an output waveform diagram of a smoothing device of the apparatus.

FIG. 9 shows the actual output signal from the smoothing device 17 when a person falls asleep. From the figure, a large signal is outputted when the rough body movement such as getting in and out from the bed, turning over and movement of hands and feet has occurred. Then, $V_a$ is set as a first set value in the comparator 7 for comparison whether the signal level of the smoothing device 17 is above $V_a$ or not. Every time when the signal level exceeds $V_a$, the measurement time is reset in the timer 8, and at the time when the signal level drops below $V_a$ thereafter a time measurement is newly started. The sleep judging means 9, judges that the body has fallen asleep when the measurement time of the timer 8 exceeds the set time $T_0$. $V_a$ may be obtained by experiments on a person being tested.

By the operation stated above, since the body movement is detected by disposing the piezo-electric element on the bedding in this working example, it is possible to detect movement of the portions which are covered by the beddings and can not be detected by the infra red-ray sensor, thus the rough body movement can be detected precisely to determine sleep. Also, since the piezo-electric element has a flexible property and is formed into a tape, it can be disposed easily on the bedding.

In the working example mentioned above, though the piezo-electric element is disposed on the mattress, it may be constructed to contain in the mattress or to dispose on the bed-frame, or further on a futon, sheet, pillow and so on, as far as they are within a range where the rough body movement can be detected.

Also, in the aforesaid working example, although one piezo-electric element was used to detect the body movement, it may be so constructed that plural piezo-electric elements are disposed on the bedding; thereby the body movement is detected by either of the piezo-electric elements even when tossing during sleep or in case of an individual difference in height, so that accuracy of detecting the body movement is improved.

Figure 10:
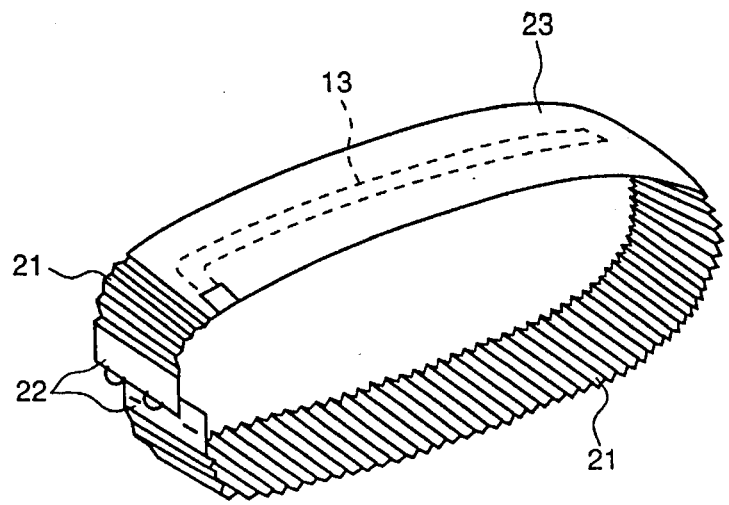
FIG. 10 is an external perspective view of body movement detecting means in a third working example of the present invention.

A third working example of the present invention will be explained in the following. This working example differs from the above-mentioned working example as shown in FIG. 10, where the piezo-electric element 13 is contained in a sheet bag 23, on the end portions of which stretchingly-and-shrinkingly movable stretch-shrink parts 21 are provided. In addition, engaging-and-disengaging parts 22, which enable engaging-and-disengaging of end tip parts by hooks, are provided respectively.

Figure 11:
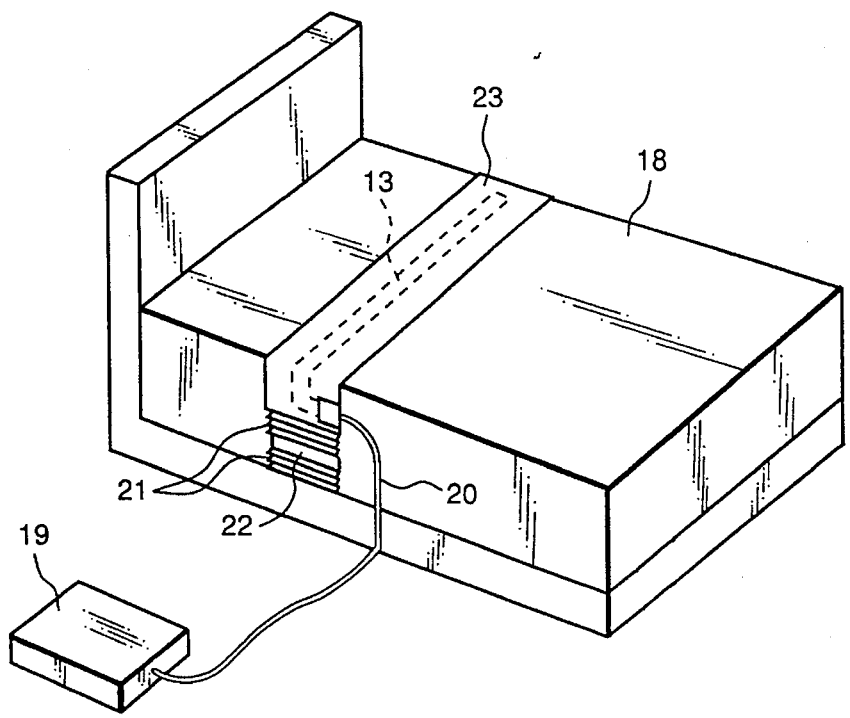
FIG. 11 is an external perspective view showing a state wherein the body movement detecting means is installed on a bed.

The configuration described above can be installed easily on any kind of bedding since the stretch-shrink parts 21 is provided. An example of installing the present working example on a bed is shown as one example in FIG. 11. It has an effect of protecting the piezo-electric element 13 from breaking even when the body moves violently on the bedding, since the impact is absorbed by the stretch-shrink parts 21. Furthermore, since the edges of the sheet 23 are removable, they can be easily fit on and removed from the bedding for washing.

Figure 12:
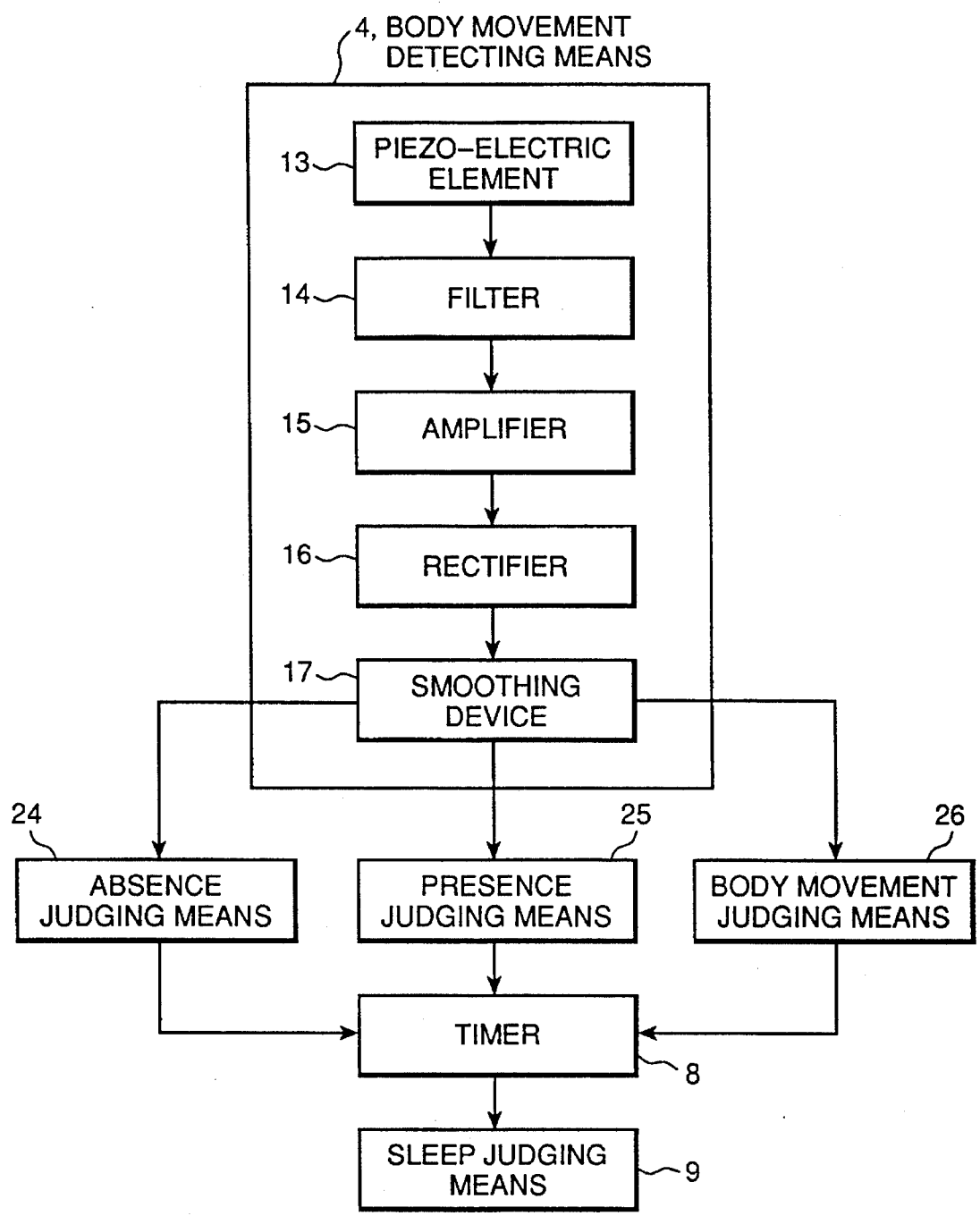
FIG. 12 is a block diagram showing a signal processing system of a fourth working sleep detecting apparatus in a fourth working example of the invention, FIG. 13($a$) is an output waveform diagram of a piezo-electric element in the second working example of the present invention, FIG. 13($b$) is an expanded output waveform diagram of a portion S of the piezo-electric element in FIG. 13($a$)

A fourth working example of the present invention will be described in the following. Difference of this working example from the above-mentioned working example is as shown in FIG. 12, where the body movement detecting means 4 is constituted by the piezo-electric element 13, filter 14, amplifier 15, rectifier 16 and smoothing device 17, like in the second working example. The fourth working example further comprises absence judging means 24 for judging absence of the body on the bed when the signal level of the smoothing device 17 is below a predetermined second predetermined set value $V_b$, presence judging means 25 for judging presence of the body on the bed in a quiet state when the signal level is above the set value $V_b$ and below a predetermined third set value $V_a$, and rough body movement judging means 26 for judging that the body is moving roughly such as turning over on the bed when the signal level exceeds the third set value $V_a$. The timer 8 resets the measurement time every time that absence is judged or rough body movement is judged, and starts time measurement when the presence is judged. Here, the third set value $V_a$ is as same as $V_a$ in the second working example. The absence judging means 24, presence judging means 25 and body movement judging means 26 are contained in the circuit unit 19.

Figure 13A:
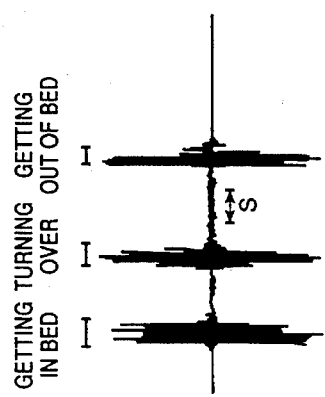
Figure 13B:
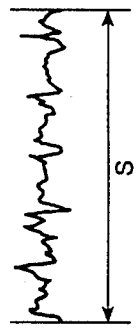

According to the configuration of this working example, the present invention is operated as follows. When the body is present on the bedding, and when the piezo-electric element 13 is deformed by the fine and rough body movements of the body, voltage is produced from the piezo-electric element responsive to a degree of deformation. An actual output signal from the piezo-electric element 13 is shown in FIG. 13(*a*) and FIG. 13(*b*). A large level signal of FIG. 13(*a*) indicates rough body movement such as getting in and out from the bed and turning over. FIG. 13(*b*) shows an expanded waveform of a portion S in FIG. 13(*a*). When the body is in bed in a quiet state, a fine body movement propagated by the fine body movement or the functioning of the heart and breathing is detected by the piezo-electric element 13 as shown in FIG. 13(*b*).

Figure 14:
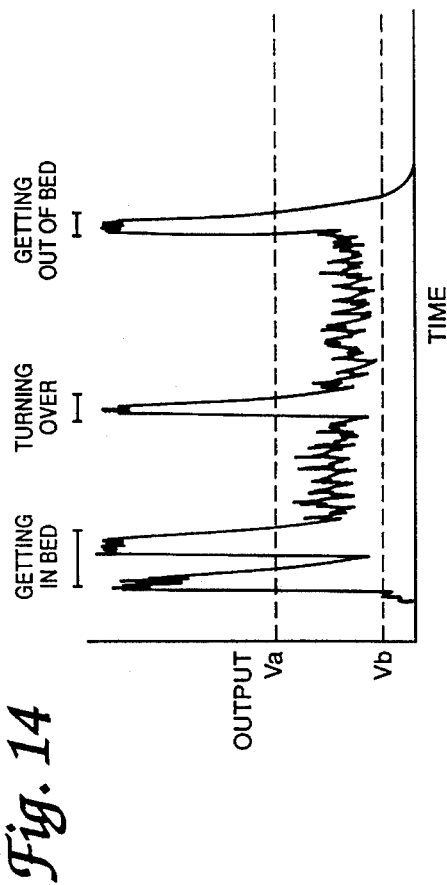
FIG. 14 is an output waveform diagram of a smoothing device in the fourth working example of the present invention.

Components of the output signal of the piezo-electric element 13 in the 1–10 Hz range are filtered by the filter 14. After that, they are amplified by the amplifier 15, rectified by the rectifier 16 smoothing device 17. FIG. 14 shows the actual output signal from the smoothing device 17 when a person falls asleep. A large signal is outputted when rough body movement such as getting in and out from the bed and turning over has occurred. In case of a quiet state besides that, a low level signal is obtained by the fine body movements stated above. When the body is absent, the signal level is zero. Based upon this, the following judgments are conducted responsive to the signal levels of the smoothing device 17. That is, when the signal level of the smoothing device 17 is below the predetermined second set value ($V_b$ in FIG. 14), the absence judging means 24 determines that the body is absent from the bed. In case the signal level of the smoothing device 17 is above $V_b$ and below the predetermined third set value ($V_a$ in FIG. 14), the presence judging means 25 determines that the body is present on the bed in a quiet state. In case the signal level of the smoothing device 17 is above $V_a$, it is judged by the body movement judging means 26 that the body on the bed has moved roughly. $V_a$ and $V_b$ can be obtained by experiments on a person being tested.

Next, when the signal from the presence judging means 25 is outputted, the time measurement operation is started by the timer 8. However, this time measurement operation is reset by the signal from the absence judging means 24 or the body movement judging means 26. Then, in the sleep judging means 9, it is judged that the body on the bed has fallen asleep when the measurement time measured by the timer 8 exceeds the set time $T_0$ previously explained.

Though the piezo-electric element is deformed to produce the voltage even when things are placed on the mattress, since there is no fine body movement due to the pulses and breathing of the body in inanimate objects, there is no occurrence of malfunction. That is, no matter who is in bed, it is possible to judge sleep as far as the fine body movement is detected. Even when impact is exerted on the bed by some action such as bed making, this is not detected as the rough body movement as far as the presence in bed is not judged.

By the above-mentioned operation, the body movement is detected by the Piezo-electric element without contacting the body, the presence in bed is judged by detecting the fine body movement of the body, and the sleep is judged from the duration of quiet state only at presence in bed. Accordingly, no matter who is in bed, sleep is judged reliably as far as the fine body movement is judged. Also, even when the impact is exerted on the bed by some actions such as placing inanimate objects like things on the bed or making bed, it is not judged as rough body movement, since presence in bed is not judged. Thus the sleep can be judged without error.

In the aforesaid working example, though the piezo-electric element is disposed on a mattress, it may be so constructed that the piezo-electric element may be contained in the mattress or on the bed-frame, or may be contained in or disposed on the futon, sheets and pillow as far as within a range of detecting the fine body movement.

Figure 15:
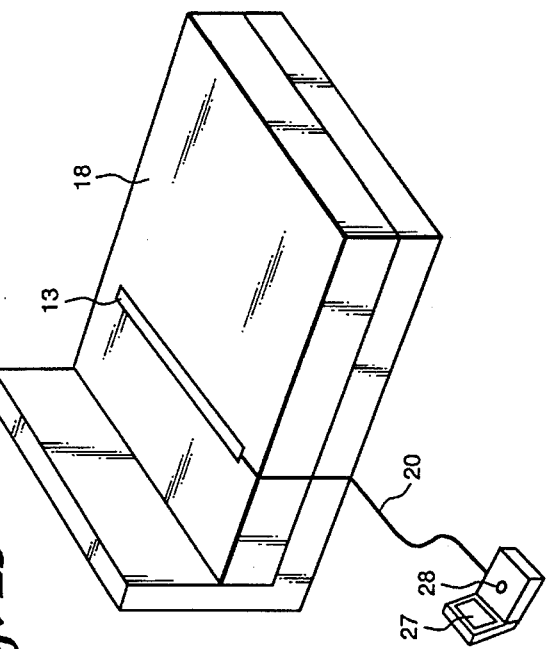
FIG. 15 is an external perspective view of a sleep detecting apparatus in a fifth working example of the present invention.

A fifth working example of the present invention will be described in the following. This working example differs from the above-mentioned working example by the inclusion of additional structure shown in FIG. 15 including display means 27 which displays the signal level of the smoothing device 17 and first setting means 28 which is capable of setting the $V_b$ and $V_a$ manually in response to the content displayed on the display means 27.

By the above configuration, the user himself can set the $V_b$ and $V_a$ manually using first setting means 18 in response to the signal level of the smoothing device 17 displayed on the display means 27. Accordingly, this allows an individual difference in the magnitude of fine body movement. The user can still select a threshold value which suits him, and therefore the fine body movement can be detected reliably to detect the sleep.

Figure 16:
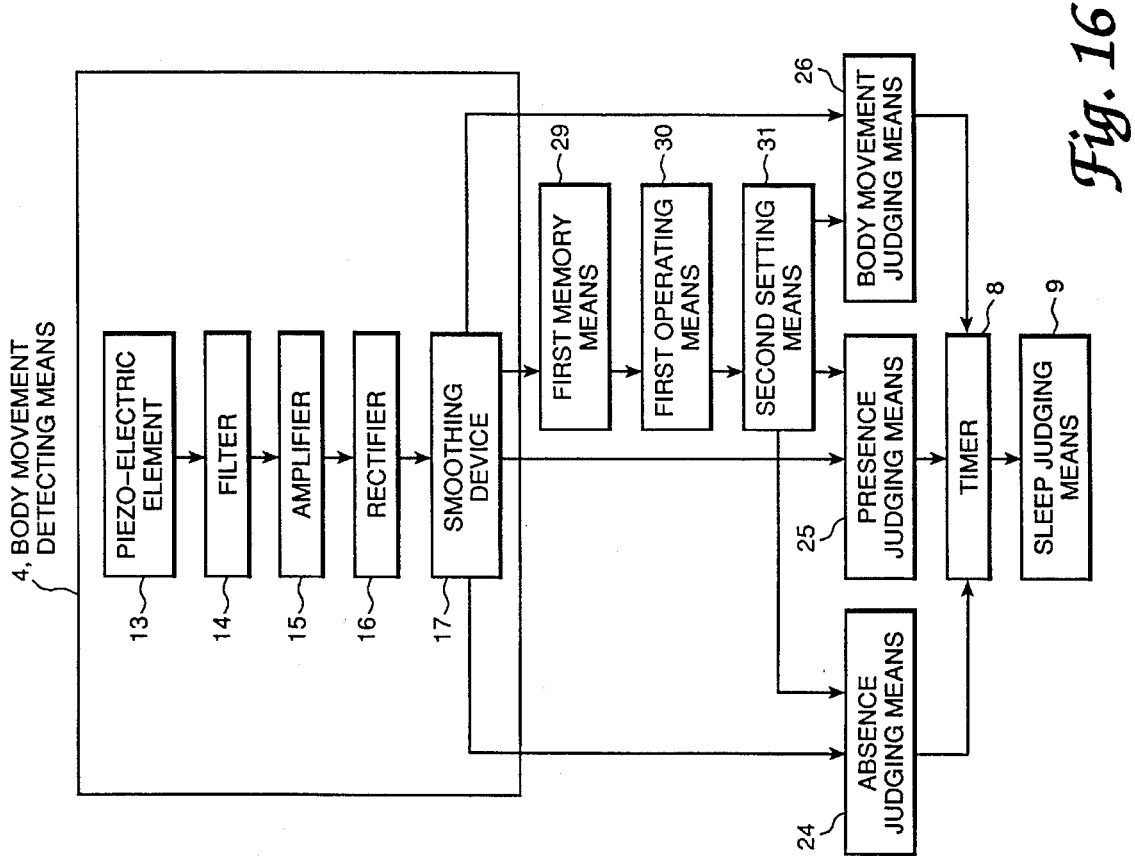
FIG. 16 is a block diagram showing a signal processing system of a sleep detecting apparatus in a sixth working example of the present invention.

A sixth working example of the present invention will be described in the following. This working example differs from the above-mentioned working examples, as shown in FIG. 16, to include first memory means 29 for sampling and storing the signal level of the smoothing device 17 of the body movement detecting means 4 at a predetermined period when the presence in bed is judged by the presence judging means 24, first operating means 30 for operating a minimum value and a maximum value of the content stored in the first memory means 29, and second setting means 31 for refreshing the minimum value as the second set value $V_b$ and the maximum value as the third set value $V_a$.

By the above-mentioned configuration, when the signal level of the smoothing device 17 is stored in the first memory means 29, the minimum value and the maximum value of the stored content are operated, and the minimum value and the maximum value are respectively represented as $V_b$ and $V_a$.

By the above-mentioned configuration, even when there are individual differences in the magnitude of fine body movements, since a set value for successively storing the magnitudes of fine body movement and detecting the fine movement is learned, the fine body movement can be detected reliably to detect the sleep.

Figure 17:
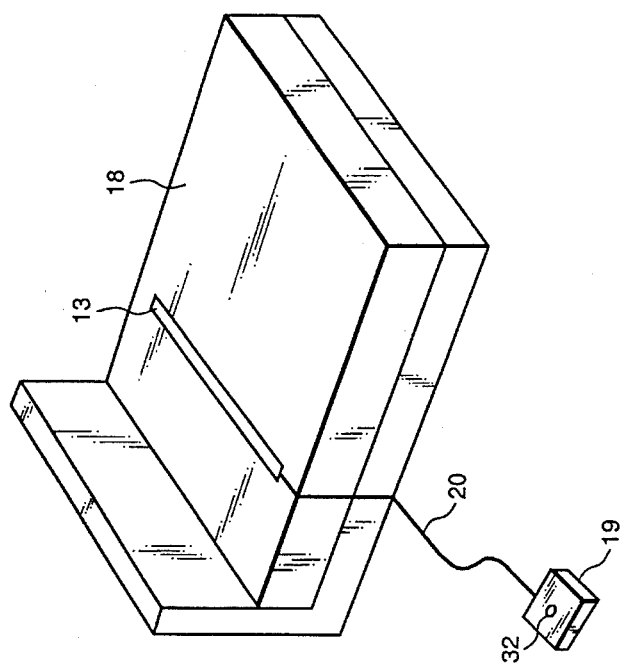
FIG. 17 is an external perspective view of a sleep detecting means in a seventh working example of the present invention.

A seventh working example of the present invention will be described in the following. Difference of this working example from the above-mentioned working example is in a point that, as shown in FIG. 17, providing third setting means 32 capable of manually changing the set time $T_0$ which has been previously explained. Thereby, even though there may be individual differences in the duration of quiet state, the sleep can be detected reliably by selecting the set time $T_0$ which fits to himself by the user.

An eighth working example of the present invention will be described in the following. Difference of this working example from the above-mentioned working example is in a point that, as shown in FIG. 18, it comprises: second memory means 33 for storing the measurement time of the timer 8 every time the time measurement of the timer 8 is reset, second operating means 34 for operating an occurrence frequency distribution of the measurement time stored in the second memory means 33, third operating means 35 for operating to obtain a certain time T in a manner that a ratio of a cumulative frequency until the time T in the said occurrence frequency distribution to a total cumulative frequency shows a predetermined value, and fourth setting means 36 for conducting the storing and operating operations at every fixed period to refresh the setting with the time T as the set time $T_0$.

By the above-mentioned configuration, the measurement time of the timer 8 is stored in the second memory means 33 every time the time measurement operation of the timer 8 is reset by the signal of the absence judging means 24 or body movement judging means 25. Then, the occurrence frequency distribution of the measurement time having been stored is operated by the second operating means 34.

Figure 19:
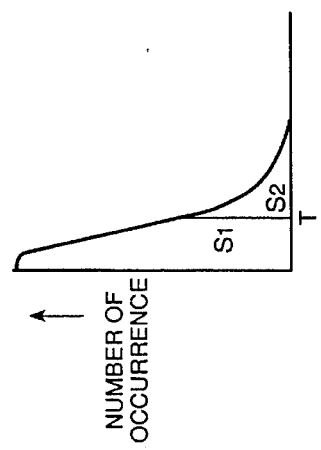
FIG. 19 is a characteristic diagram showing a frequency distribution of the body movement quiescent time.

FIG. 19 shows the operation of frequency distribution. In the figure, the abscissa is graduated by measurement time, and the ordinate is graduated by frequency. Next, in the occurrence frequency distribution, the time T is operated by the third operating means 35 in a manner that a ratio of a cumulative frequency until a certain time to a total cumulative frequency (S1/(S1+S2) in FIG. 19) shows a predetermined value $S_0$. Then, the time T is set by the fourth setting means 36 as the set time $T_0$. The value $S_0$ can be obtained by experiment on various subjects.

Thereby, even when there are individual differences in durations of quiet state, the sleep can be detected reliably, since the duration of quiet state is successively stored and the set time for detecting the sleep is learned.

Figure 20:
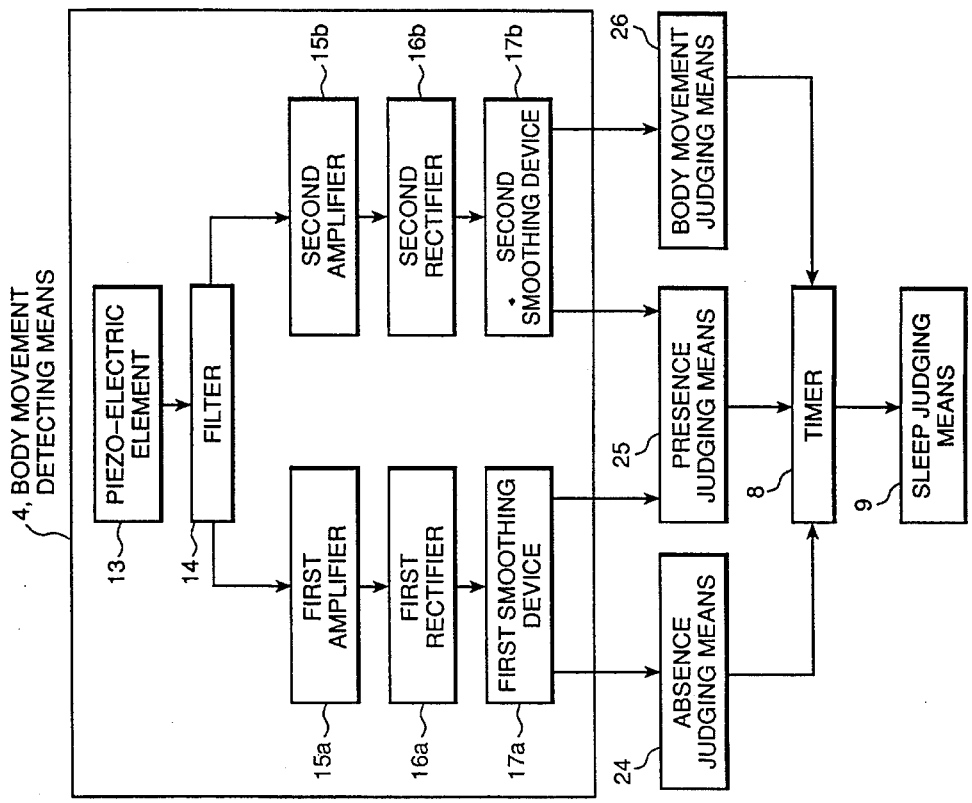
FIG. 20 is a block diagram of a sleep detecting apparatus in a ninth working example of the present invention, FIG. 21($a$) is an output waveform diagram of a first smoothing device of the apparatus, FIG. 21($b$) is an output waveform diagram of a second smoothing device of the apparatus.

A ninth working example of the present invention will be described in the following. Difference of this working example from the above-mentioned working example is in a point that, as shown in FIG. 20, the body movement detecting means 4 comprises: at least one piezo-electric element 13 disposed on the bedding, a filter 14 which filters a certain specific frequency component for respective signals of the piezo-electric element 13, a first amplifier 15a which amplifies the signal from the filter 14, a second amplifier 15b which amplifies the signal from the filter 14, a second amplifier 15b having a smaller amplification than the first amplifier 15a and amplifying the signal from the filter 14, a first rectifier 16a, a second rectifier 16b, a first smoothing device 17a which smoothes the signal from the first rectifier 16a, and a second smoothing device 17b which smoothes the signal from the second rectifier 16b; whereby the absence judging means 24 judges the absence of a body on the bedding when the signal level of the first smoothing device 17a is below the second set value $V_b$, the presence judging means 25 judges the presence of a body on the bedding in a quiet state when the signal level of the first smoothing device 17a is above $V_b$ and the signal level of the second smoothing device 17b is below a fourth set value $V_c$ predetermined, and the rough body movement judging means 26 judges the rough body movement of the body on the bedding when the signal level of the second smoothing device 17b is above $V_c$.

Figure 21A:
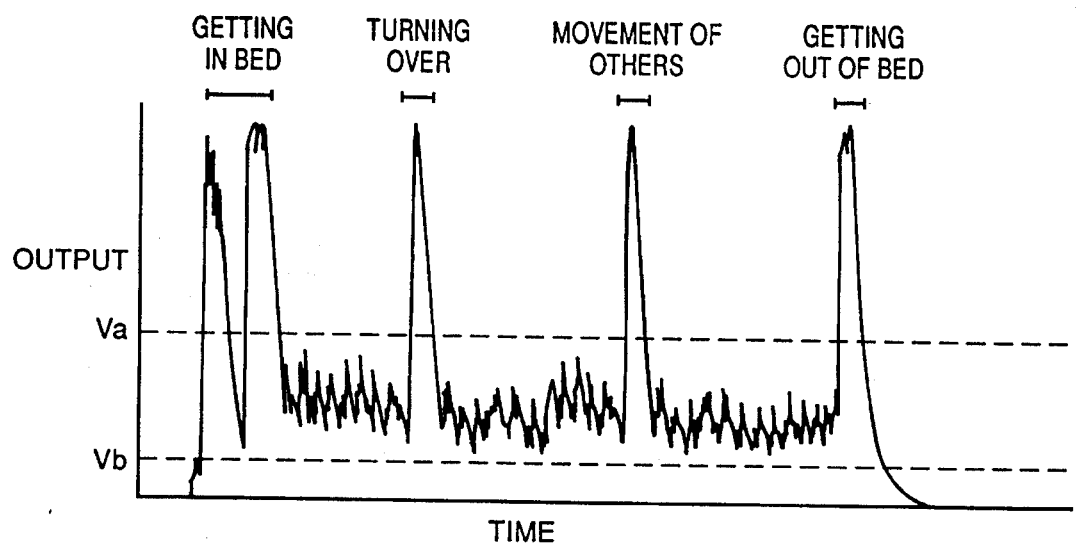
Figure 21B:
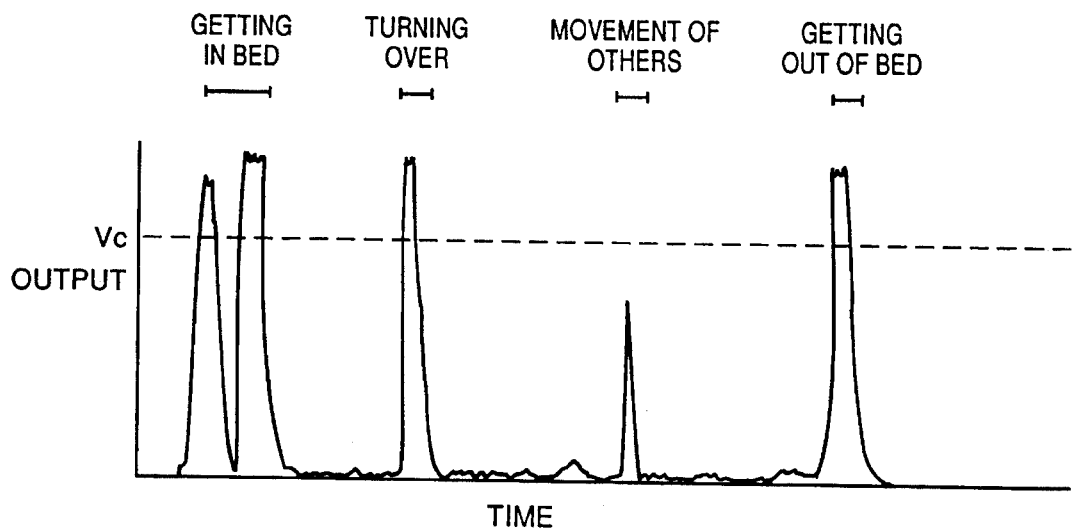

According to the configuration of this working example, the present invention operates as follows. In case the body is present on the bedding and when the piezo-electric element 13 disposed on the bedding is deformed by the fine or rough movement of the body, a voltage is produced from the piezo-electric element responsive to a degree of deformation. This output signal is filtered by the filter 14 and the signal is amplified by the first amplifier 15a, rectified by the first rectifier 16a and smoothed by the first smoothing device 17a, and further amplified by the second amplifier 15b, rectified by the second rectifier 16b and smoothed by the second smoothing device 17b. Here, the first amplifier 15a has a same characteristic as the amplifier 15 of the conventional example previously described, and the second amplifier 15b has the amplification set smaller than that of the first amplifier 15a. And, the two smoothing devices respectively have the same characteristics as the rectifier and integrator of the conventional examples previously described. FIG. 21(a) shows a signal waveform of the first smoothing device 17a at actual sleep, and FIG. 21(b) shows a signal waveform of the second smoothing device 17b. Here. though the magnitude of deformation applied to the piezo-electric element 1 by both the rough body movement of the body in bed and movement of other is naturally larger in the former, since the first amplifier 15a has as same high amplifying characteristic as the amplifier in the conventional example previously described as shown in FIG. 21(a), the signal level by the rough body movement such as getting in and out of the bed and turning over and the signal level by movement of other are both above the first set value $V_a$ described before; and the rough movement of the body in bed and the movement of other can not be distinguished. However, since the amplification of the second amplifier 15b is set smaller than that of the first amplifier 15a, the signal level of the movement of other is smaller as compared with the rough body movement of the person in bed as shown in FIG. 21b; and thus when the fourth set value $V_c$ is set as shown in the figure, it is possible to distinguish the rough body movement of the person himself in bed and the movement of other.

Thereby, the following judgments are made responsive to the signal levels of the first smoothing device 17a and the second smoothing device 17b. In case the signal level of the first smoothing device is below $V_b$, it is judged by the absence judging means 24 that the body is absent on the bedding. In case the signal level of the first smoothing device 17a is above $V_b$ and the signal level of the second smoothing device 17b is below $V_c$, it is judged by the presence judging means 25 that the body is present on the bedding in a quiet state.

In case he signal level of the second smoothing device 17b is above $V_c$, it is judged by the body movement judging means 26 that the body on the bedding has produced rough body movement. Next, when the signal is outputted from the presence judging means 25, the time measurement operation is started by the timer 8. However, the time measurement operation is reset by the signal of the absence judging means 24 or the body movement judging means 26. And, in the sleep judging means 9, when the measurement time described measured by the timer 8 exceeds the set time $T_0$ before, it is judged that the body has fallen asleep on the bedding.

By the above-mentioned operation, according to this working example, by adding an amplifier having a smaller amplification than the conventional example in signal processing circuit of the sleep judgment of the conventional example, the vibration propagation by the body movement of the person in bed and movement of other can be distinguished, thus it is possible to provide a sleep detecting apparatus without malfunction in judging the sleep.

Figure 22:
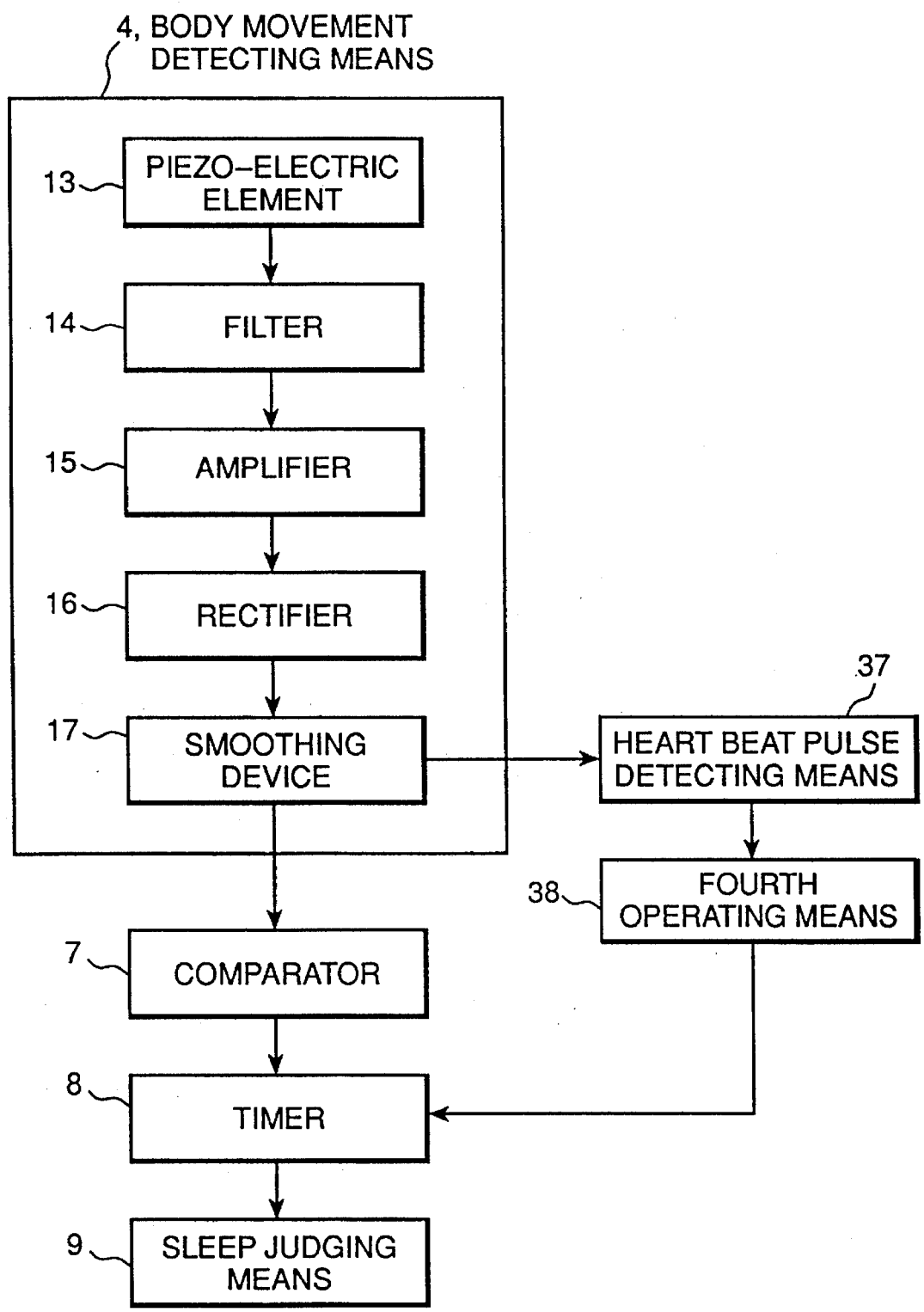
FIG. 22 is a block diagram of a sleep detecting apparatus in a tenth working example of the present invention.

A tenth working example of the present invention will be described in the following. Difference of this working example from the above-mentioned working example is in a point that, as shown in FIG. 22, the body movement detecting means 4 is constituted by the piezo-electric element 13, filter 14, amplifier 15, rectifier 16 and smoothing device 17 as the second working example, and has the pulse rate detecting means 37 which detects and counts pulses by the signal from the smoothing device 17; whereby the fourth operating means 38 which operates the change in pulse rate within a predetermined time, and that the timer 8 resets the measurement time and starts the new time measurement every time the signal level of the smoothing device 17 exceeds a predetermined fifth set value and an operation value of the fourth operating means 38 exceeds a predetermined sixth set value.

Figure 23:
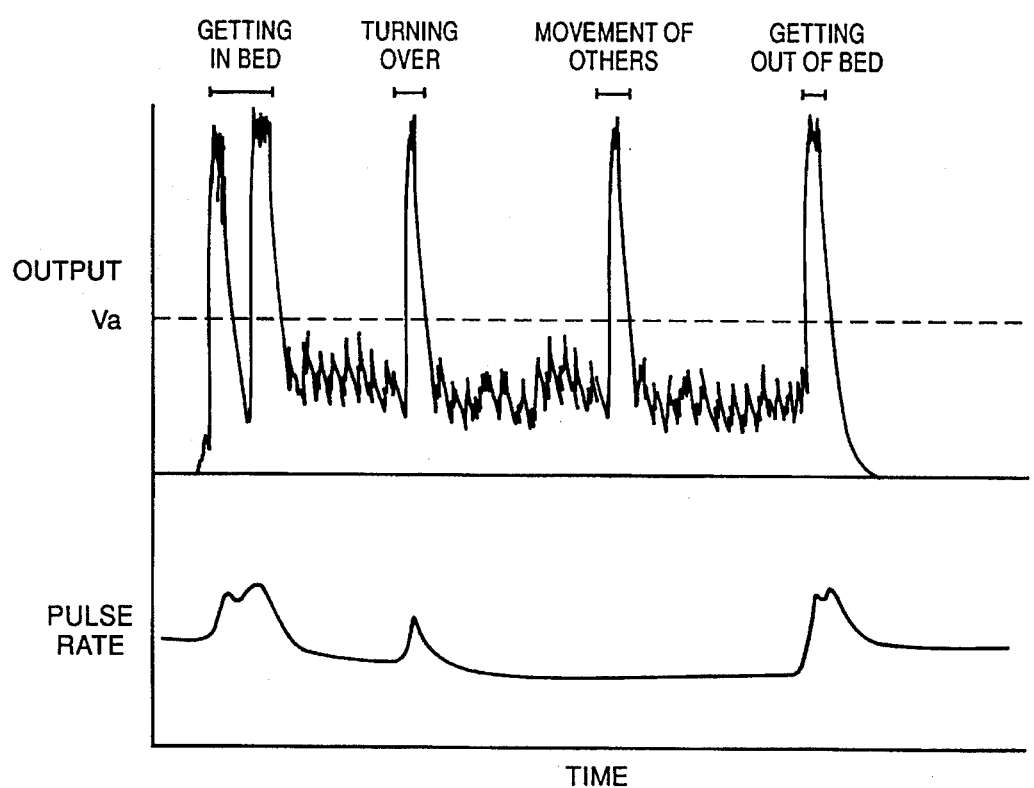
FIG. 23 is an output waveform diagram smoothing device and pulse rate detecting means of the apparatus.

According to the configuration of this working example, the present invention operates as follows. The absence, presence and rough body movement are judged by the signal level of the smoothing device 17 similarly to the above-mentioned working example, but as shown in FIG. 12b and FIG. 13, it is possible to detect heart beat pulses of the human body, and by the pulse detecting means 37 the heart beat pulses are detected and counted from the signal of the smoothing device. Hereupon, when the rough body movement such as turning over is produced for the human body as shown in FIG. 23, a signal of large level is outputted from the smoothing device 17, and a transient heart beat pulse rate increase by the rough body movement is noticed. Meanwhile, though a signal of large level is outputted when others walk around the bed, there is no increase of pulse rates in the person in bed. Accordingly. it is possible to distinguish motion of other and the rough body movement of the person in bed when the increase of pulse rates at rough body movement is detected. Therefore, the change in pulse rates within a predetermined time is operated by the fourth operating means 38 with respect to the pulse rates which are detected by the pulse rate detecting means 37; and the measurement time is reset and the new time measurement is started in the timer 8, every time the signal level of the smoothing device 17 exceeds the fifth set value $V_a$ and the operation value of the fourth operating means 38 exceeds a sixth set value predetermined. Thereby, only when the rough body movement is produced by the person in bed, the time measurement is reset and the new time measurement is started. Then, in the sleep judging means 9, when the measurement time measured by the timer 8 exceeds the afore-mentioned set time $T_0$, it is judged that the body has fallen asleep on the bedding. Here, the fifth set value $V_a$ is as same as $V_a$ in the second working example.

By the operation of the above-mentioned, by detecting the transient increase of pulse rates noticed when the rough body movement is produced on the person in bed, it is possible to distinguish motion of other in the vicinity of bed and the rough body movement of the person in bed, thereby the malfunction of aging the sleep is solved.

Figure 24:
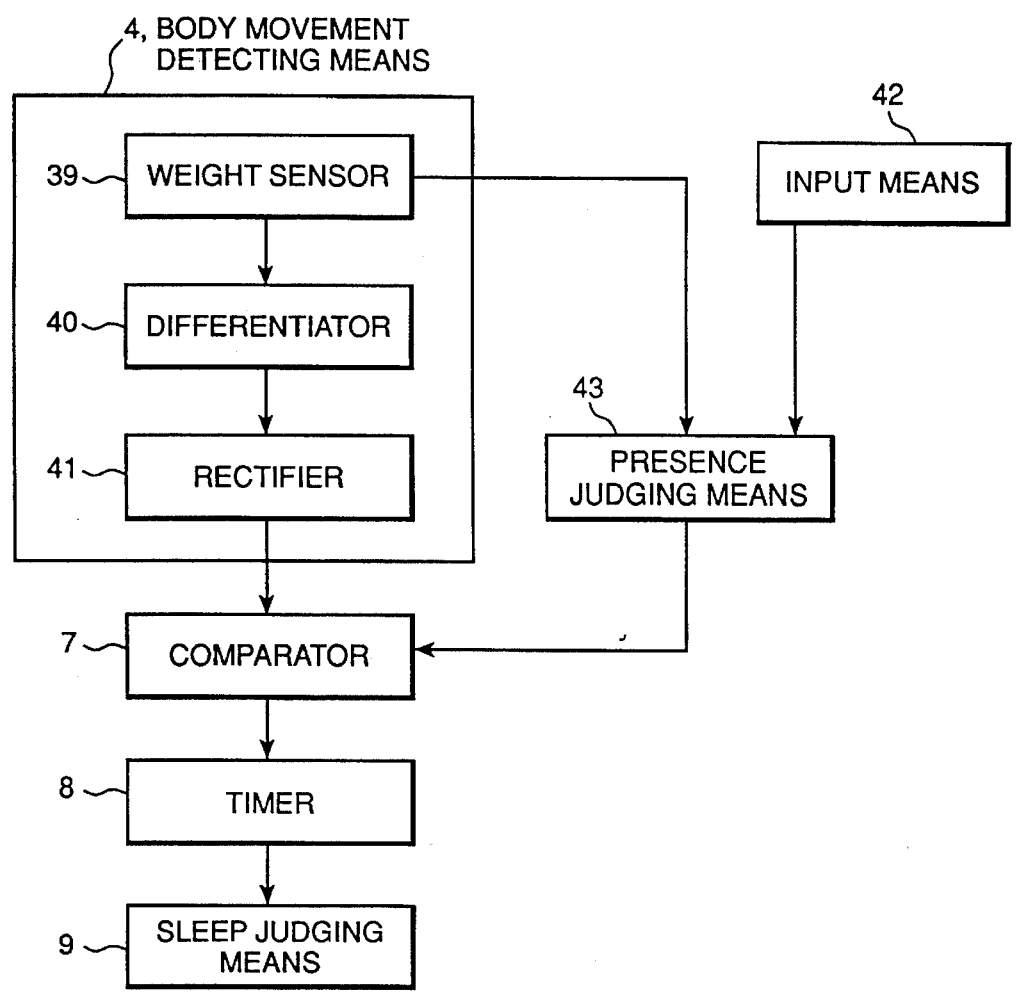
FIG. 24 is a block diagram of a sleep detecting apparatus in an eleventh working example of the present invention, and FIG. 25 ($a$) and ($b$) is an output waveform diagram of a weight sensor of the apparatus.

An eleventh working example of the present invention will be described in the following. Difference of this working example from the working example aforementioned is the body movement in that, as shown in FIG. 24, detecting means 4 consists of: a weight sensor 39 using a load-cell, a differentiator 40 which differentiates the signal of the weight sensor 39, a rectifier 41 which rectifies the signal from the differentiator 40, input means 42 for inputting weight of the person in bed, and presence judging means 43 which judges that the person is present in bed when the weight detected by the weight sensor 39 is within a fixed range around the value inputted from the input means 42. The weight sensor 39 is installed on the bed frame.

Figure 25A:
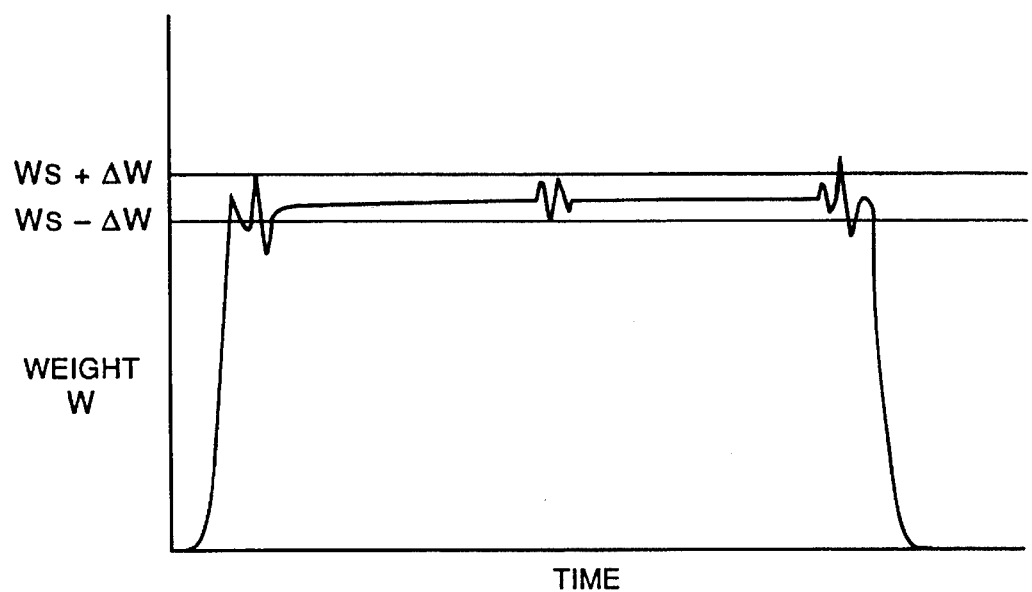
Figure 25B:
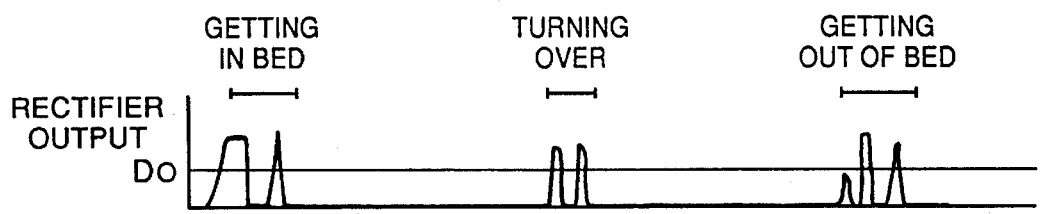

By the configuration stated above, when the user inputs weight $W_s$ in advance by the input means 41, it is judged by the presence judging means 43 that the person is present in bed, in case the weight W detected by the weight sensor 39 is within a fixed range (Ws±AW) around the value $V_s$ inputted by the input means 42 as shown in FIG. 25 In case the Presence in bed is judged, since the signal of the weight sensor 39 changes temporarily when the rough body movement is produced on the person in bed, it is compared in the comparator 7 whether or not the value of signal level D of the differentiated and rectified value of the signal is above the predetermined threshold value $D_0$. Every time the signal level D exceeds the threshold value $D_0$, the timer 8 resets the time measurement taking as that the rough body movement is produced; and at the point of time when the signal level becomes below the threshold value $D_0$, newly starts the time measurement. And, in the sleep judging means 9, it is judged that the human body has fallen asleep when the measurement time of the timer 8 exceeds the afore-mentioned set time $T_O$. In case a person other than the person to be in bed gets in the bed or things are placed on the bed, the detecting operation of sleep is not performed since the presence in bed is not judged. Also, even when the impact is exerted on the bed by some action such as bed making, it is not detected as the rough body movement as far as the presence in bed is not judged.

By the above-mentioned operation, weight of the person in bed is detected by the weight sensor to judge the presence and the rough body movement of the person in bed is detected to judge the sleep only in case of the presence in bed, and therefore in case a person other than the person in bed gets in the bed or things are placed on the bed, the presence is not judged and the operation for detecting the sleep is not performed. And, even when the impact is exerted on the bed by some action such as bed making, it is not detected as the rough body movement as far as the presence is not judged. Accordingly, it is possible to judge sleeping without error in such a way that the sleep is judged only in the case the person is in bed.

In the above working example, though the piezo-electric element was disposed on the bedding, the detection may be made by a construction that the piezo-electric element is disposed on furniture such as a sofa and a study chair to detect the sleep. Also, the piezo-electric element may be disposed on a toilet seat and a bath tub to detect the sleep.

While the working example of the present invention has been described above, as fields of application of the present invention there are so many besides aforementioned; for example, it may be applied widely and used practically as a control signal of an air conditioner, lightings and video and audio equipment for realizing a comfortable sleeping environment, or used as measuring instruments for sleeping experiments in clinical filed such as a medical treatment of insomnia, or used as monitoring equipment for sleeping management and bed management in hospital and at-home case.

INDUSTRIAL APPLICABILITY

As described hereinabove, according to a sleep detecting apparatus of the present invention, the following effects can be obtained.

Since the body movement is detected by an infra red-ray sensor without contacting to the body, and sleep is judged from a simple variable such as a duration of quiet state wherein the rough body movement is stopped, it is possible to detect the sleeping easily without installing detecting means for detecting a movement of eyes and pulse wave on the human body, and without contacting thereto as in the past.

Also, since the body movement is detected by disposing a piezo-electric element on the bedding, it is possible to detect movement of the portions covered by the bedding which can not be detected by the infra red-ray sensor, thus the rough body movement is detected reliably to judge the sleep.

Also, since the piezo-electric element has a flexible property and is formed into a tape, it can be easily disposed on the bedding.

Besides, a sheet piezo-electric element, which is provided, on respective end portions, with stretchingly-and-shrinkingly movable stretch-shrink parts, and besides, engaging-and-disengaging parts which enable engaging-and-disengaging of the end tip parts, is contained inside, and therefore it can be installed easily on any beddings, and the piezo-electric element can be prevented from breaking, since the impact is absorbed by the expansion even when the body moves violently on the bedding.

Also, the body movement is detected without contacting to the human body by the piezo-electric element, the fine body movement is detected to judge the presence in bed, and sleep is judged from the duration of quiet time only in case of the presence in bed, and therefore the sleep is judged no matter who is in bed as far as the fine body movement is detected. And even when the impact is exerted on the bed by some action such as placing an inanimate object like things or bed making, it is not detected as the rough body movement as far as the presence in bed is not judged, and thus it is possible to judge the sleep without malfunction.

Since setting means whereby the user can set a set value for optionally detecting the body movement is provided taking into account of an individual difference in the magnitude of body movement, the body movement can be detected more reliably to detect the sleep.

Moreover, since the magnitude of body movement is successively stored and a set value for detecting the body movement is obtained by the learning, taking into account of an individual difference in the magnitude of body movement, it is possible to detect the body movement more reliably to detect the sleep.

Also, since setting means whereby the user can set a set time value of the body movement quiescent time optionally is provided, taking into account of an individual difference in the quiescent time of the body movement, it is possible to detect the sleep more reliably.

Furthermore, since a frequency distribution of the body movement quiescent time is operated to obtain a set time value of the body movement quiescent time, taking into account of an individual difference in the quiescent time of the body movement, the sleep can be detected more reliably.

Also, by adding an amplifier having a smaller amplification than the conventional example in a signal processing circuit of the sleep judgment, it is possible to distinguish vibration propagations by the body movement of the person in bed and the action by others, thus a sleep detecting apparatus without malfunction in judging the sleep can be provided.

By detecting a transient rise of pulse rates noticed when the rough body movement is produced on the person in bed, it is possible to distinguish movement of other in the vicinity of bed and the rough body movement of the person in bed, thereby malfunction of the sleep judgment is solved.

Furthermore, since weight of the person in bed is detected by a weight sensor thereby to judge the presence in bed, and the rough body movement of the person in bed is detected thereby to judge the sleep only in the case of presence in bed, in case the other person gets in bed or things are placed on the bed, the presence is not judged and the operation for detecting the sleep is not conducted. Also, even when the impact is exerted on the bed by some action such as bed making, it is not detected as rough body movement as far as the presence in bed is not judged. Accordingly, it is possible to judge sleeping without error such as detecting the sleep only when the person is in bed.

What is claimed is:

1. An apparatus which operates to sense a condition indicative of sleep, comprising:

an infrared ray emitter and sensor assembly for radiating infrared rays over a bed on which a human body is located, and for detecting a characteristic of infrared rays and for outputting a detection signal which is generated by said characteristic and indicative of moving of said human body, said detection signal being proportional to an amount of movement of said human body;

a comparator for comparing said detection signal to a predetermined value indicative of rough body movement;

a timer for measuring a time interval during which said human body is in a substantially motionless condition on the basis of said detection signal, said time interval being interrupted when a level of said detection signal exceeds said predetermined value, said substantially motionless condition indicating that said human body is asleep, and sleep judging means for outputting an electrical signal indicating that said human body is asleep when said time interval exceeds a predetermined time period.

2. A sleep detecting apparatus in accordance with claim 1, wherein said assembly is mounted on one of said bed and a wall.

3. A sleep detecting apparatus in accordance with claim 1, wherein said predetermined time period is between 10 and 15 minutes.

4. A sleep detecting apparatus in accordance with claim 1, wherein said detection signal is representative of infrared light reflected from said human body to said assembly.

* * * * *

UNITED STATES PATENT AND TRADEMARK OFFICE
CERTIFICATE OF CORRECTION

PATENT NO. : 5,479,939
DATED : January 2, 1996
INVENTOR(S) : OGINO

It is certified that error appears in the above-indentified patent and that said Letters Patent is hereby corrected as shown below:

ON THE TITLE PAGE:

"[63]    Continuation of Ser. No. 784,438, Dec. 20, 1991, abandoned."

should read:

--[63]   Continuation of Ser. No. 784,438, Dec. 20, 1991, abandoned, which was the national stage of international application number PCT/JP91/00307, filed March 7, 1991.

Signed and Sealed this

Sixth Day of August, 1996

Attest:

BRUCE LEHMAN

Attesting Officer    Commissioner of Patents and Trademarks